United States Patent [19]

Kay

[11] Patent Number: 4,723,946
[45] Date of Patent: Feb. 9, 1988

[54] URINARY CATHETER, HYGIENE SYSTEM AND PROCESS THEREFOR

[76] Inventor: Dennis M. Kay, 1188 Omaha Cir., Palm Harbor, Fla. 33563

[21] Appl. No.: 828,538

[22] Filed: Feb. 12, 1986

[51] Int. Cl.[4] .................... A61M 25/00; A61M 27/00
[52] U.S. Cl. ..................................... 604/267; 604/53; 604/247; 604/249
[58] Field of Search .................. 604/53, 27, 30–32, 604/39–43, 48, 82, 83, 151, 181, 246–249, 267, 266

[56] References Cited

U.S. PATENT DOCUMENTS

| | | | |
|---|---|---|---|
| 2,243,299 | 5/1941 | Travers | 604/39 |
| 3,331,371 | 7/1967 | Rocchi et al. | 604/246 |
| 3,583,404 | 6/1971 | McWhorter | 604/247 |
| 3,780,736 | 12/1973 | Chen | 604/32 |
| 3,926,187 | 12/1975 | Iglesias | 604/248 |
| 4,227,533 | 10/1980 | Godfrey | 604/247 |
| 4,502,502 | 3/1985 | Krug | 604/247 |
| 4,512,764 | 4/1985 | Wunsch | 604/83 |
| 4,563,173 | 1/1986 | Ledley | 604/83 |
| 4,585,436 | 4/1986 | Davis et al. | 604/83 |
| 4,604,093 | 8/1986 | Brown et al. | 604/248 |

Primary Examiner—Stephen C. Pellegrino
Assistant Examiner—Ralph Lewis
Attorney, Agent, or Firm—Lalos & Keegan

[57] ABSTRACT

A novel urinary catheter, hygiene unit and daily process for cleansing this catheter while in place within the user's bladder. This equipment and process are intended to reduce the occurrence of urinary tract infections and associated sepsis in individuals with chronic, long-term indwelling urinary catheters. Pressurized fluids delivered through a specially configured catheter dislodge, rinse and remove bacteria and bacterial growth medium formed by mucus, crystalline urinary deposits and urinary debris from the inner aspect or urinary lumen of the catheter. Special safety features of the catheter provide for a separation of the inner aspects of the catheter from the bladder lumen while the cleansing process is occuring and prevent attachment of the hygiene unit to the catheter unless this separation is accomplished. These safety features prevent the introduction of cleansing fluids into the user's body. The hygiene unit accomplishes this cleansing process by pumping sterile water and cleansing fluids in an orderly predetermined sequence at the required flow rates, volumes and composition. The hygiene unit is equipped with a "Unit" function so that it can clean itself and also a safety function, so that it shuts itself off when its fluid reservoirs are empty.

53 Claims, 19 Drawing Figures

URINARY CATHETER, HYGIENE SYSTEM AND PROCESS THEREFOR

BACKGROUND OF THE INVENTION

A urinary catheter is a tube passed through the urethra or abdominal wall (suprapubic catheter) and into the bladder. Urinary catheters have been in use for the drainage of the bladder for many years. Over 40 years ago the last major development in urinary catheters was introduced, the Foley Catheter. The Foley Catheter has an inflatable balloon at its distal end which allows the catheter to be held within the bladder.

There is a significant major drawback associated with the use of current urinary catheters. Urinary catheters, especially when used on a chronic basis, are associated with a markedly increased incidence of urinary tract infection. Urinary tract infection can take the form of cystitis, pyelonephritis and in the immunocompromised patient, older or particularly debilitated individuals these urinary tract infections can result in the development of systemic sepsis and even death. Identification of the cause or factors associating urinary catheterization and increased rates of urinary tract infections has been illusive. To date, the actual factors causing increased rates of urinary tract infections in patients with urinary catheters has not been identified. Probably as a consequence, the medical products industry has been unable to provide a urinary catheter that is associated with a lower incidence of urinary tract infections.

Length of time of catheterization has been associated with an increasing frequency and severity of urinary tract infections. Therefore, although widely used on a chronic basis, urinary catheters are currently not recommended for chronic use. As yet, no clear evidence has been established to identify the cause or factors relating chronic urinary catheterization to the associated increased rates of urinary tract infection.

As noted above, length of time of catheterization is associated with increased frequency and severity of urinary tract infections. Many patients with long term urinary catheterization develop a state of chronic or relatively constant urinary tract infection. Although the factors responsible for markedly increased rates of urinary tract infection in patients with chronic urinary catheterization have not been identified, clinical observation has shown certain similarities in catheterized patients who develop urinary tract infection. These clinical observations reveal common elements among these chronically catheterized patients when they are hospitalized with acute urinary tract infection. Frequently these patients have the same urinary catheter in place for weeks or even months. The appearance of the urinary catheters withdrawn from these patients is usually remarkably similar: The lumen and inner surfaces of the catheter, is found to be coated with an adherent yellow concentration. This concretion is found to be composed of crystalline urinary deposits, mucus, protien and cellular debris mostly composed of bladder epithelial cells and white blood cells. The concretion also contains significant amounts of bacteria. This concretion or coating on the inner surfaces of the urinary catheter withdrawn from a patient who has had long term urinary catheterization provides an excellent medium for continued bacterial growth, especially in the presence of urine and body heat. This concretion or coating is generally not found on the external surface of the chronis indwelling urinary catheter.

It is proposed that the inner surface or lumen of the urinary catheter provides a location for the adherence and accumulation of this coating. The inner surface of the urinary catheter is less accessable to the body's natural processes for cleansing and resistance to infection. Being less accessable to the body's natural cleansing processes, over time the interior of the urinary catheter becomes coated with the described concretion and provides an excellent medium for bacterial growth and the development of urinary tract infection.

The subject invention is designed to provide a solution to the problem of increased incidence of urinary tract infections in patients with chronis urinary catheterization. The subject design is expected to allow the chronic or long term use of urinary catheterization with decreased rates of urinary tract infection and associated sepsis. This development should have significant impact on the health and longevity of individuals requiring chronic urinary catheterization. In addition, decreased rates of infection will provide shortened hospital stays. The subject invention, by reducing occurence of infection, should provide a reduction of the total number of hospital inpatient days required for individuals with urinary tract infections and associated sepsis. Reduction of urinary tract infection frequency and severity, as well as decreased requirements for antibiotics in patients with urinary catheterization will therefore provide remarkable savings in health care expenditures.

Based on clinical experience with a daily cleansing system for urostomy equipment (Stoma Hygiene System and Process Therefor, patent pending, U.S. Patent and Trademark Office, Ser. No. 731,897), it is proposed that daily cleansing of the inner aspect of a chronic indwelling urinary catheter will prevent accumulation of the described coating. This daily cleansing will therefore eliminate the excellent substrate for the development of urinary tract infection. The subject invention provides a method for the daily cleansing of the inner aspect or lumen of indwelling urinary catheters, without requiring the removal of the urinary catheter from the patient's bladder. The subject method is advantageous for several reasons: the interior of the indwelling urinary catheter can be cleansed without daily removal or changing of the urinary catheter, a process that would be cost prohibitive from the standpoint of equipment and health care personnel costs and inconvenient for the patient as the process of urinary catheterization should be done using a sterile or aspetic technique; and the process of daily removal of a urinary catheter is quite uncomfortable for the patient and potentially damaging to the epithelium of the urethra.

The subject invention proposes a method for the daily cleansing of the inner aspects of chronic indwelling urinary catheters, without requiring removal of the urinary catheter from the patient. It is proposed that the subject method of daily catheter hygiene will eliminate the substrate that facilitates formation of urinary tract infections. The proposed method should therefore markedly reduce the occurence and severity of urinary tract infections in patients with chronic indwelling urinary catheters.

OBJECT OF THE INVENTION

Accordingly, it is the principal object of the present invention to provide a novel urinary catheter designed to allow daily cleansing of this catheter, while it remains in the user's bladder.

Another object is to provide a novel hygiene unit for cleansing urinary catheters.

A further object is to provide a novel cleansing process for urinary catheters.

A still further object is to provide a novel arrangement that prevents the introduction of catheter cleansing fluids into the user's body.

Other objects and advantages of the present invention will become more apparent to those persons having ordinary skill in the art to which the present invention pertains from the following description taken in conjunction with the accompanying drawings.

DESCRIPTION OF THE INVENTION

The present invention provides for a novel method and regimen for the daily cleansing of the urinary lumen of an indwelling urinary catheter, specifically designed for this purpose. It is intended that this daily cleansing process can be performed without removing the catheter from the patient's bladder and without exposing the patient's bladder to potentially irritating foreign substances. It is proposed that this process of daily cleansing of the inner or urinary lumen of an indwelling urinary catheter will markedly reduce occurence and severity of urinary tract infections in patients requiring chronic or long term urinary catheterization. As noted above, this process requires a specially designed urinary catheter and a correspondingly specially designed catheter hygiene unit. Both the urinary catheter and its corresponding catheter hygiene unit will be described herein.

Description of the Urinary Catheter

Figures 1, 2:
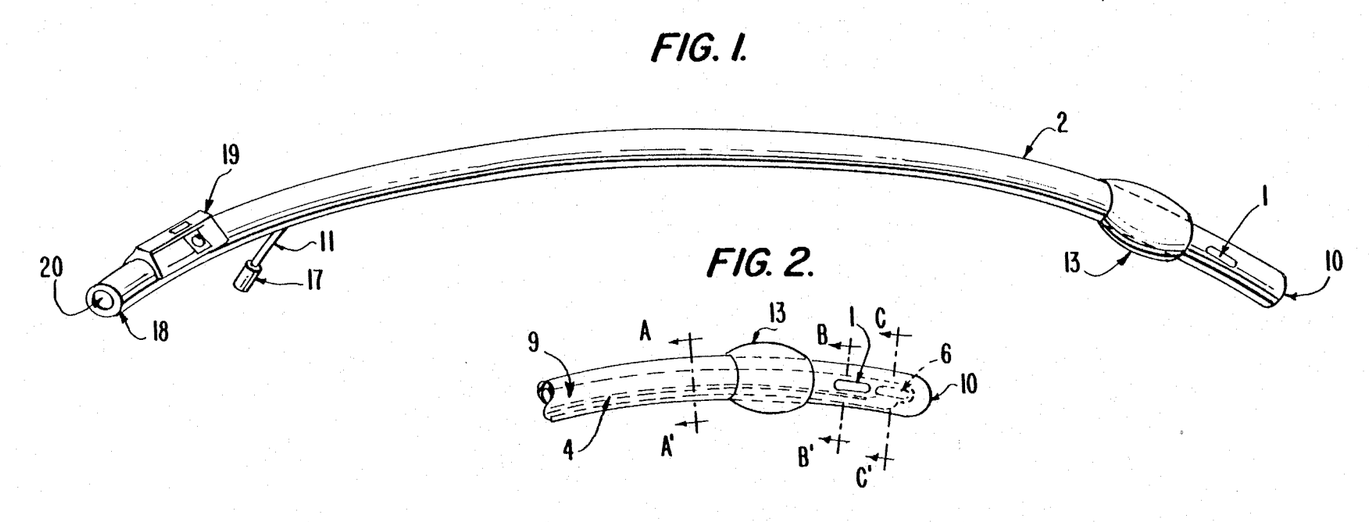
FIG. 1 is a perspective view of the urinary catheter of the present invention.
FIG. 2 is a plan view of the distal portion of the catheter shown in FIG. 1.
Figure 5:
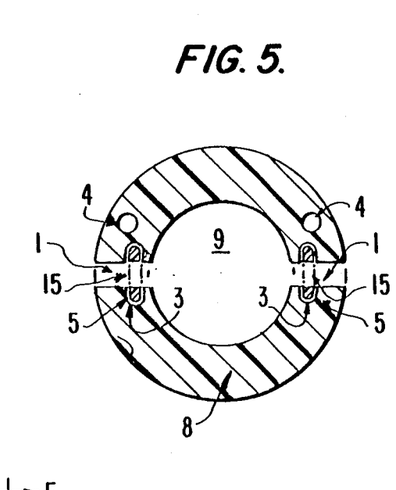
FIG. 5 is an enlarged cross section view of the catheter taken at line B—B' in FIG. 2.

The subject urinary catheter is made of a soft, flexible and biologically inert synthetic material such as Silastic. As shown in FIG. 1, the subject catheter has a generally cylindrical shape with an open proximal end 18 and a closed distal end 10. The catheter's distal end 10 is placed in the patient's urinary bladder either by the suprapubic approach or more commonly, by passing the catheter, distal end first, through the patient's urethral meatus and along the urethra until the distal end of the catheter enters the patient's urinary bladder. Successful catheterization of the urinary bladder is indicated by discharge of urine from the urinary lumen opening 20 at the proximal end 18 of the catheter. Just proximal to distal end 10, the catheter has two longitudinally arranged urine inflow ports 1, demonstrated in FIGS. 1, 2 and 3. These urine inflow ports 1 are openings through the wall 8 of the catheter and allow the contents of the urinary bladder to enter the main or urinary lumen 9 of the catheter, as shown in FIG. 5, during the utilization of the catheter in its usual urinary drainage mode.

Figure 3:
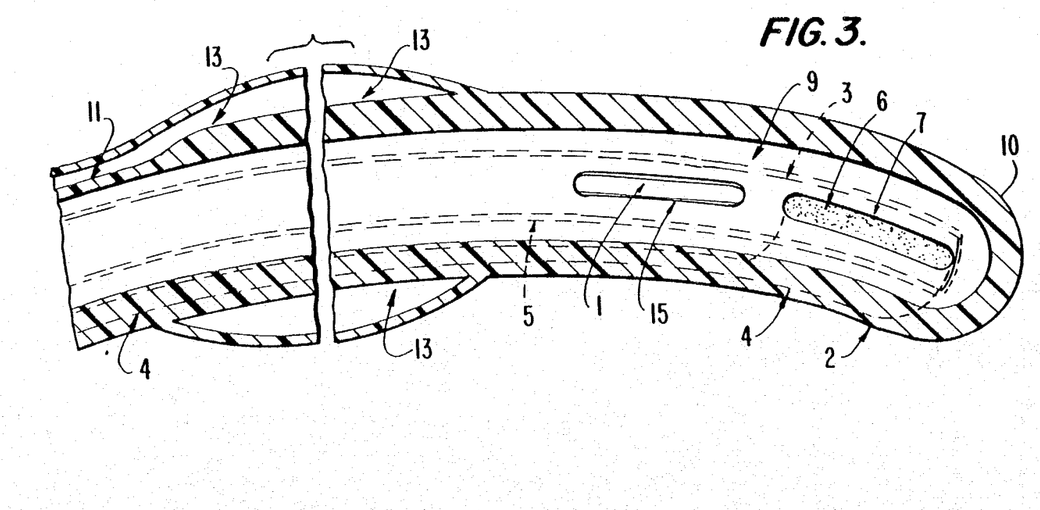
FIG. 3 is an enlarged longitudinal tranverse section of the distal tip of the catheter shown in FIG. 2.
Figure 4:
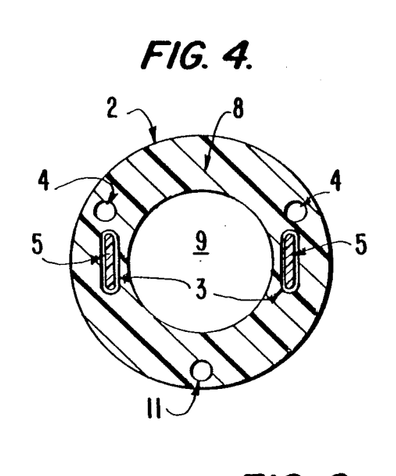
FIG. 4 is an enlarged cross section view of the catheter taken at line A—A' in FIG. 2.

Located proximally to the urine inflow ports 1 at the catheter's distal end 10 is the catheter's circumferential balloon 13 that is inflated after the catheter has been successfully placed in the urinary bladder. Balloon 13 inflates to a large enough diameter to hold the distal end of the catheter in the patient's bladder. The catheter balloon 13 is inflated using a one-way twist luer tip compatible valve 17 located at proximal end 18. Valve 17 communicates with balloon inflation lumen 11 located within the catheter's wall 8, as shown in FIG. 3. A standard luer tip syringe filled with saline is attached to valve 17 and saline is injected along lumen 11 to fill balloon 13.

At the catheter's proximal end 18 the catheter's main or urinary drainage lumen 9 can be attached at proximal opening 20 via a standard conical universal tubing adapter to appropriate drainage tubing and receptacle.

Figure 7:
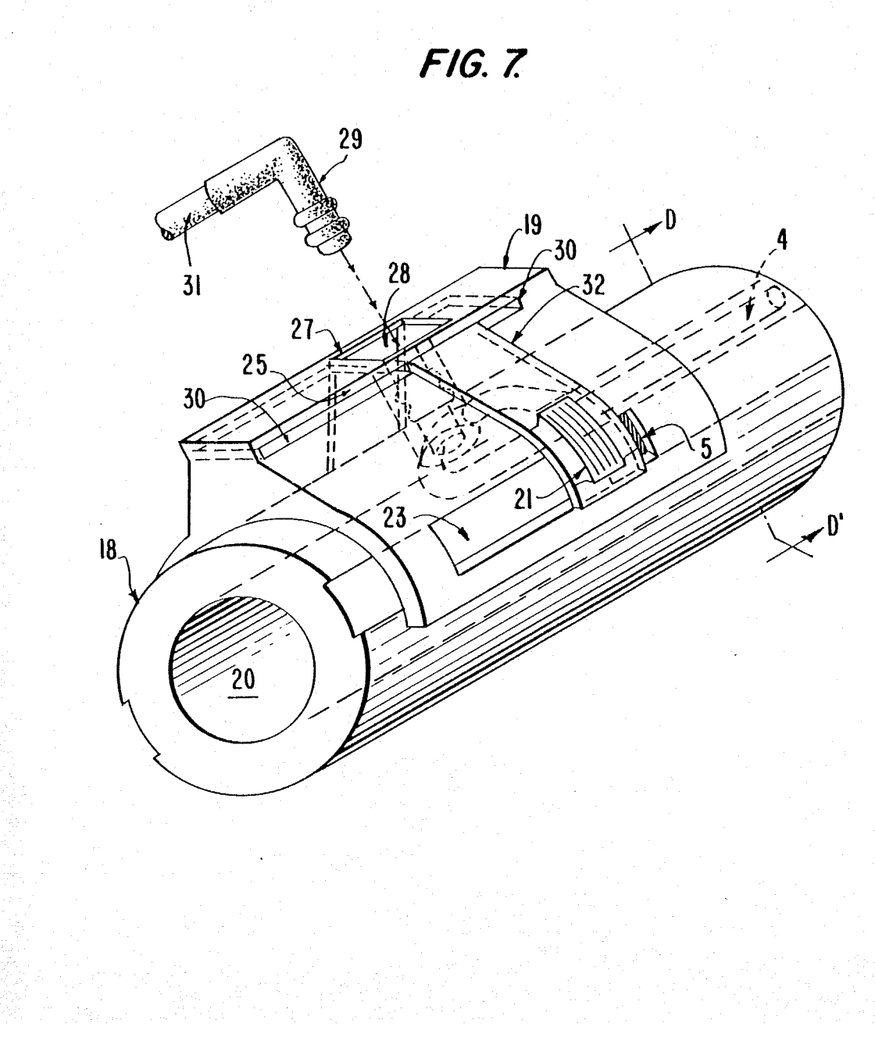
FIG. 7 is an enlarged isometric view of the proximal portion of the catheter as shown in FIG. 1 with hatch cover forward.
Figure 8:
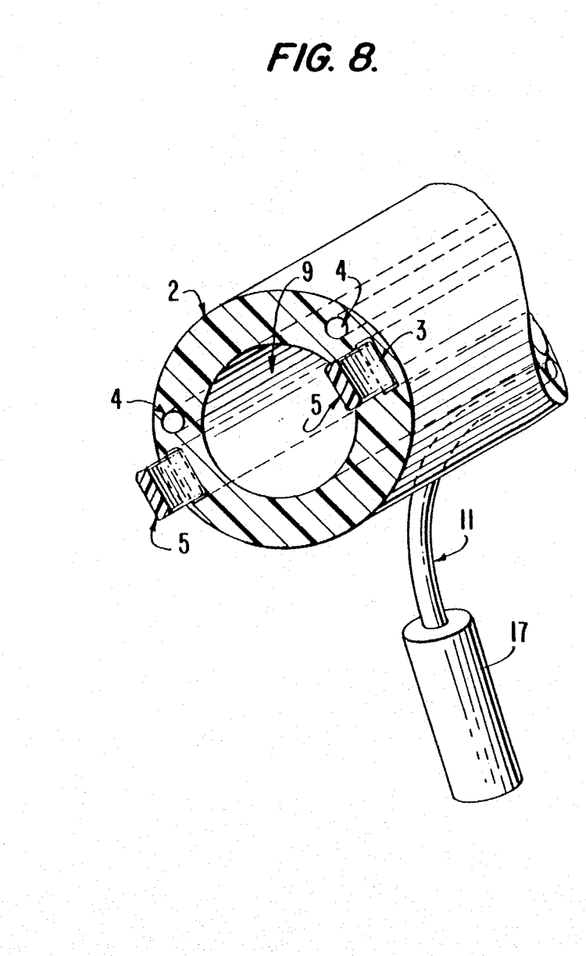
FIG. 8 is an enlarged isometric cross section view of the catheter taken at line D—D' in FIG. 7.

Located at the catheter's proximal end 18 is the housing 19 for the hygiene unit connection assembly, shown in detail in FIG. 7. The hygiene unit connection assembly allows attachment of the subject urinary catheter to the corresponding catheter hygiene unit 40 to be subsequently described herein. The catheter hygiene system is a unique device for daily hygiene of urinary or other catheters, not proposed in the prior art. The design of the connection assembly between the hygiene unit and the urinary catheter provides for an important and unique safety feature of the present invention. The catheter hygiene unit can not be attached to the urinary catheter during the catheter's urinary drainage function. The urinary catheter cleansing process can not occur unless the urine inflow ports 1 are closed and the urinary lumen 9 is separated from communication with the inner aspect of the urinary bladder. This separation of the urinary lumen 9 of the urinary catheter from the inner aspect of the bladder during the cleansing process insures that the cleansing process can be performed without removing the catheter from the patient's bladder and without exposing the patient's bladder to potentially irritating foreign substances.

Figure 6:
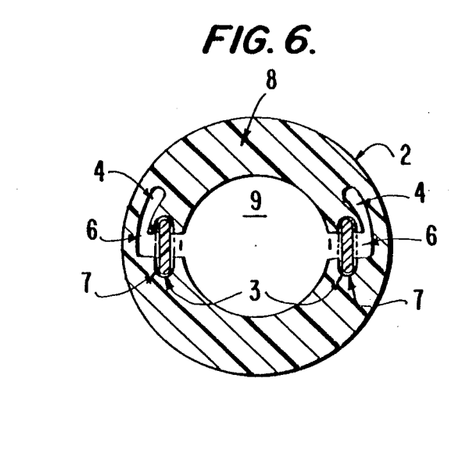
FIG. 6 is an enlarged cross section view of the catheter at line C—C' in FIG. 2.
Figure 13:
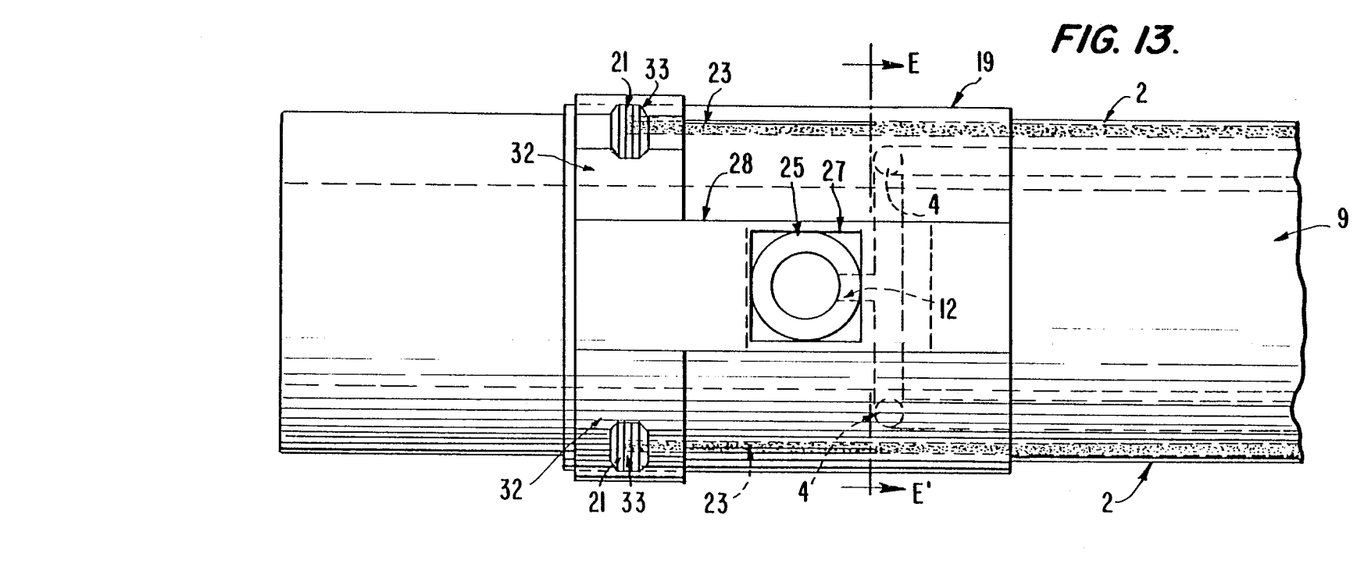
FIG. 13 is a top plan view of the proximal portion of the catheter with port occlusion slide and hatch cover highlighted.

The hygiene unit connection assembly housing 19 has in its upper surface a hatch 27. Through hatch 27 the receptor 25 for the catheter hygiene unit connector 29 can be accessed. A hatch cover 28 is mounted in the slides along grooves 30 in the upper aspect of the housing 19. The hatch cover 28 is attached to finger tabs 21 via housing slide 32. Housing slide 32 is also integrally attached to the proximal end of the urine inflow port occlusion slide 5 shown in FIG. 7 and delineated in FIG. 13. FIGS. 3, 5 and 6 demonstrate the functions of the urine inflow port occlusion slide 5. The urine inflow port occlusion slide 5 can be moved proximally or distally along its containing channel 3 by operation of the finger tabs 21 on housing slides 32. When the finger tabs 21 are placed in their most distal position along slot 23 and groove 30 the urine inflow port occlusion slides 5 are in their corresponding most distal position in channel 3. At this distal position, as shown in FIGS. 3 and 5, the urine inflow port occlusion slides' apertures 15 correspond with the urine inflow port 1 and allow drainage of bladder contents through urine flow ports 1 into the main urinary lumen 9 of the catheter. At this described distal position of the urine inflow port occlusion slide 5, subject urinary catheter can function in its urinary drainage mode and the cleansing function of the catheter system can not proceed. Because when slides 5 are in their most distal position, hatch cover 28 in hosing 19 is positioned to prevent access throug hatch 27 to receptor 25 by the hygiene unit connector 29, as shown in FIG. 7. In this distal position, the urine inflow port occlusion slides' 5 distal ends 7 are positioned so as to occlude and block access to the inflow ports 6 of the cleansing solution inflow channels 4 as shown in FIG. 6. Thus urinary contamination of the cleansing solution inflow channel 4 during the catheter's urinary drainage function is prevented. Also, the influx of cleansing solution into the urinary lumen 9 of the subject catheter is prevented, when the urine inflow ports 1 are open, as shown in FIGS. 3 and 5. This position of slide 5 allows communication between the inner aspects of the urinary bladder and the main or urinary lumen 9. The introduction of potentially irritating cleansing solution into the urinary bladder is prevented by providing a safety feature at each end of the urinary catheter.

Figure 9:
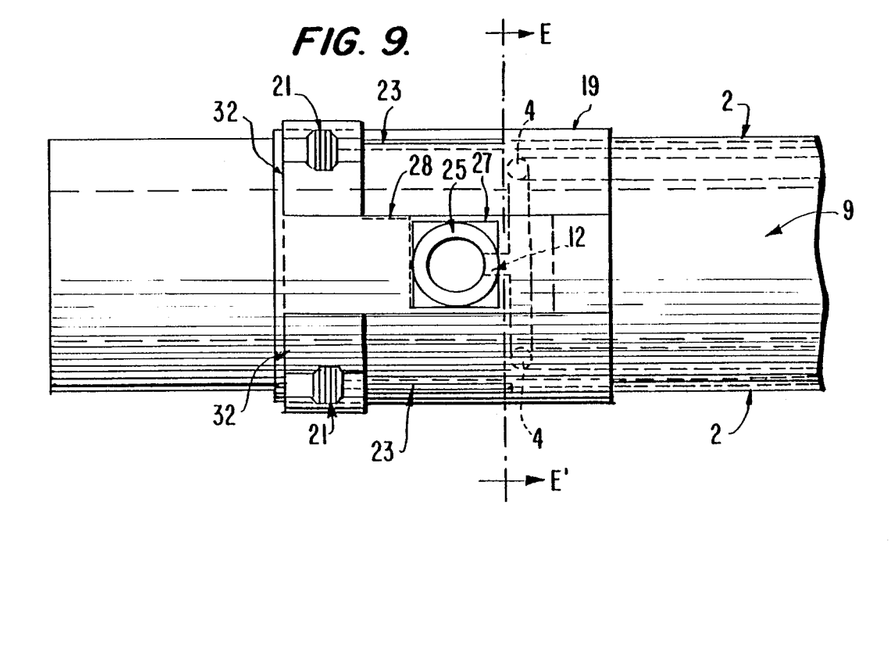
FIG. 9 is an enlarged top plan view of the proximal portion of the catheter as shown in FIG. 1 with hatch cover retracted.
Figure 10:
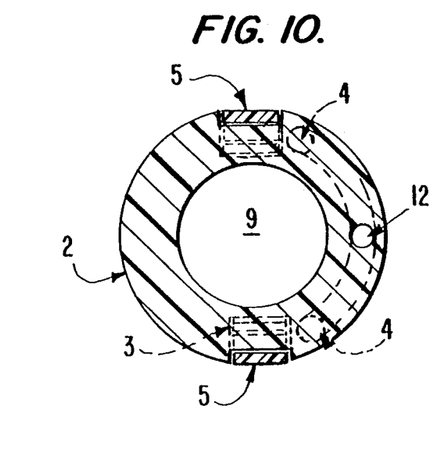
FIG. 10 is an enlarged cross section view of the catheter taken at line E—E' in FIG. 9.
Figure 11:
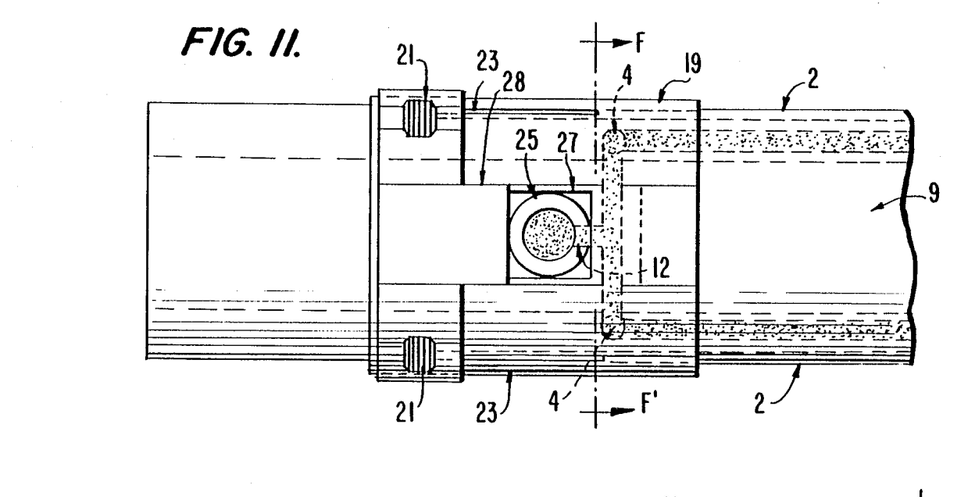
FIG. 11 is a top plan view of the proximal portion of the catheter with the cleansing system highlighted.
Figure 12:
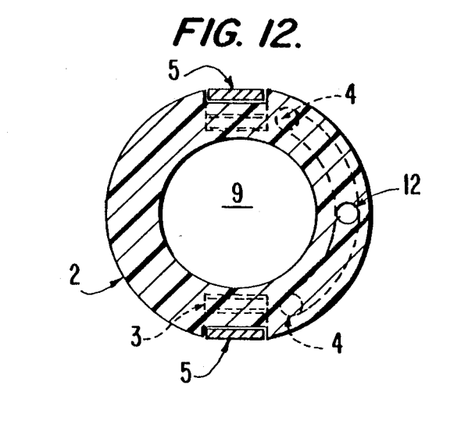
FIG. 12 is an enlarged cross section of the catheter taken at line F—F' in FIG. 11 demonstrating channels for cleansing solution inflow.

When the housing slide 32 is moved with use of finger tabs 21 to the slide's most proximal location along grooves 30 and slot 23, the urine inflow port occlusion slide 5 is also brought to its most proximal position within channel 3. At this most proximal position, the distal portion 7 of the urine inflow port occlusion slide 5 is positioned directly over the urine inflow ports 1, preventing inflow of urinary bladder contents through urine inflow ports 1 and thereby effectively separating the internal lumen of the patient's urinary bladder from the urinary lumen 9 of the subject catheter. As the distal portion 7 of the urine inflow port occlusion slide 5 is drawn proximally along channel 3, the inflow port 6 of the channels 4 for cleansing solution inflow are opened and the catheter is prepared for its cleansing mode. As demonstrated in FIGS. 9 and 11, when the housing slide 32 is drawn proximally along slot 23 and groove 30 the hatch cover 28 is drawn proximally along groove 30, opening hatch 27 in the upper surface of housing 19, providing access to receptor 25 for the hygiene unit connector 29. This retraction of hatch cover 28 and exposure of access to receptor 25 prepares the catheter for the hygiene mode, as demonstrated in FIG. 13.

The hygiene mode is begun by insertion of the hygiene unit connector 29 through hatch 27 into double grooved receptor 25. The catheter system is now prepared for completion of the catheter hygiene mode. During the catheter hygiene mode a variety of specified solutions are pumped at appropriate volumes and flow rates from catheter hygiene unit 40 through hygiene unit outflow hose 31 into its attached connector 29. Cleansing solutions flow from the hygiene unit through hose 31 into connector 29, through connector 29 and into receptor 25. From receptor 25 these cleansing solutions flow into the communicating channel 12 and thereby into the contiguous cleansing solution inflow channels 4 as demonstrated in FIG. 11. The cleansing solutions proceed along cleansing solution inflow channels 4 to port 6 at the distal end of the catheter as shown in FIGS. 3 and 6. Since the urine inflow port occlusion slide 5 has been placed in its proximal position to allow for progression of the catheter cleansing mode, the cleansing solution inflow ports 6 communicate directly with the main urinary lumen 9 of the subject catheter and allow the flow of cleansing solutions into the urinary lumen 9 of the catheter. Note that the distal portions 7 of urine inflow port occlusion slides 5 occlude port 1 and prevent any leakage of these cleansing solutions from the lumen 9 of the catheter into the patient's bladder. The cleansing solutions flow through the entire length of the catheter's urinary lumen 9 from distal to proximal end, draining out of the catheter into the appropriate drain hose and collection device via opening 20 at the catheter's proximal end 18. At the completion of the cleansing mode, connector 29 is withdrawn from receptor 25 and hatch cover 28, slides 32, finger tabs 21 and urine inflow port occlusion slides 5 are all returned to their distal position; closing hatch opening 27 and opening urine inflow ports 1, while occluding cleansing solution inflow ports 6. Thus the catheter is returned to its urinary drainage mode.

Description of the Catheter Hygiene Unit

Figure 14:
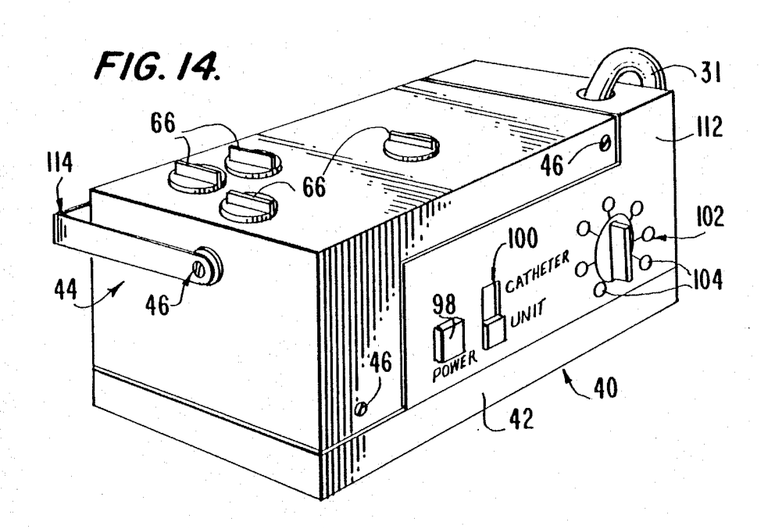
FIG. 14 is a perspective view of the catheter hygiene unit of the present invention.
Figure 15:
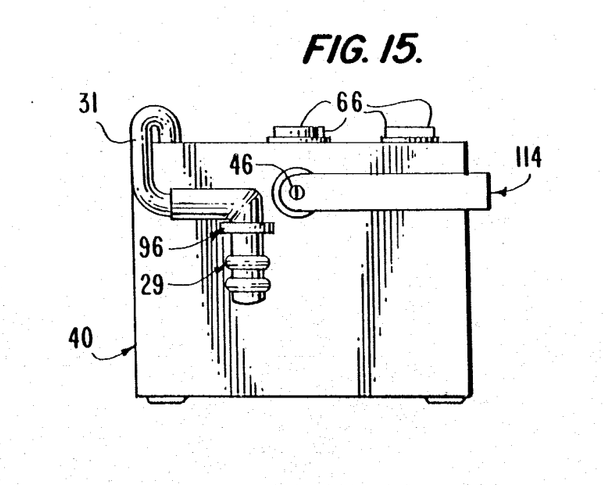
FIG. 15 is a side view of the unit shown in FIG. 14.

A specially-designed electrically powered catheter hygiene unit shown generally at 40 in FIG. 14 pumps pressurized fluids at the desired fluid compositions, fluid flow rates, volumes, and pulse rates to cleanse urinary catheter main lumen 9. Hygiene unit 40 comprises a unit base 42 and an external housing 44 secured to the unit base by a plurality of nylon screws 46 inserted through corresponding base unit threaded tabe 48.

Figure 16:
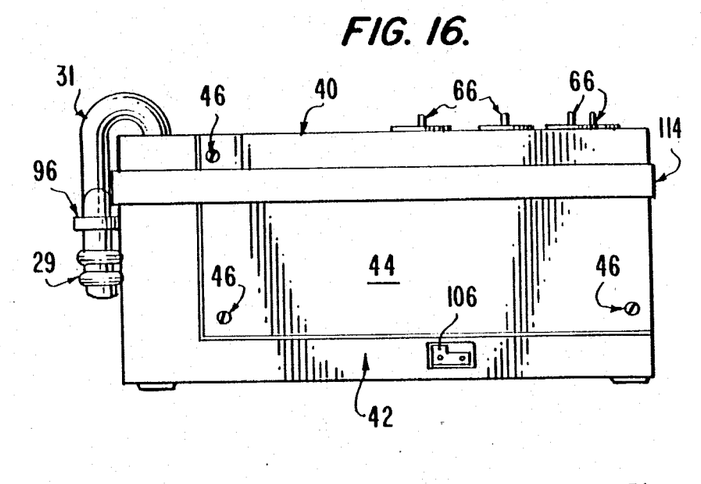
FIG. 16 is a rear view of the unit shown in FIG. 14.
Figure 17:
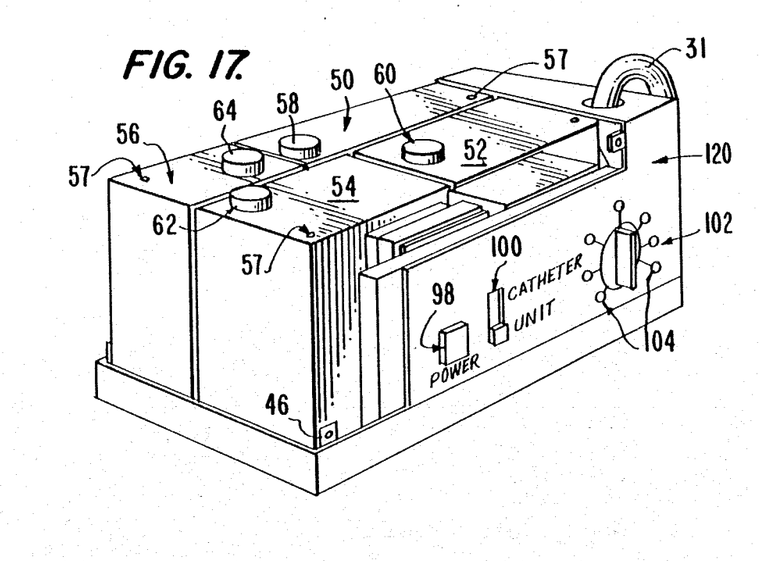
FIG. 17 is a perspective view of the unit of FIG. 14 with external housing removed.
Figure 18:
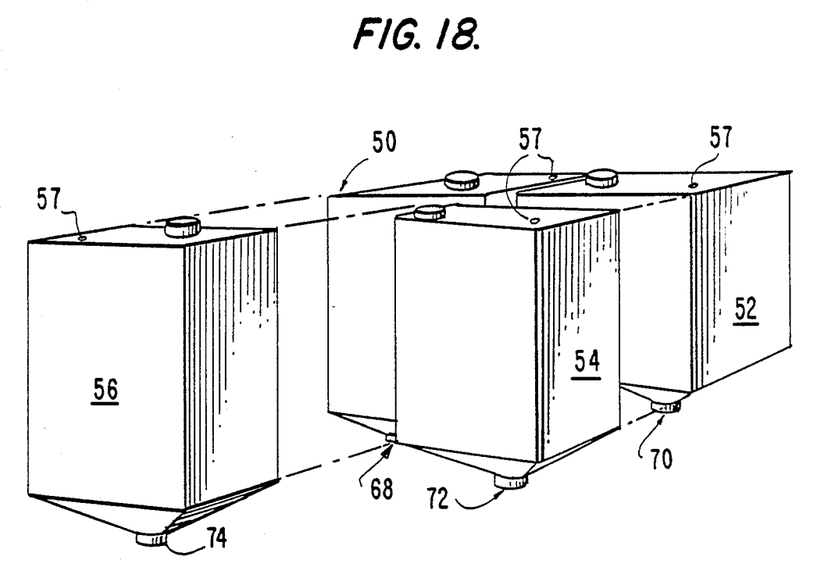
FIG. 18 is a perspective view of the reservoirs of the unit shown in FIG. 14.

Base unit 42 supports a five hundred milliliter water reservoir 50, a two hundred fifty milliliter antiseptic solution reservoir 52, a two hundred milliliter solubilizing agent reservoir 54, and a one hundred seventy-five milliliter mucolytic agent reservoir 56. To facilitate reservoir emptying, the upper surface of each reservoir has a small vent opening 57. The reservoirs are nested together on the unit base 42 as best shown in FIG. 17 and each has its own filling port 58, 60, 62 and 64, respectively, with threaded port plugs 66. Water reservoir 50 has a discharge port 68 exiting from the bottom thereof into the receptor 78 in the unit base 42. Antiseptic solution reservoir 52 has a discharge port 70 exiting from the bottom thereof into the receptor 80 in the unit base 42. Solubilizing agent reservoir 54 has a discharge port 72 exiting from the bottom thereof into the receptor 82 in the unit base 42. Mucolytic agent reservoir 56 has a discharge port 74 exiting from the bottom thereof into the receptor 84 in the base unit 42. All reservoir discharge ports and corresponding receptors are demonstrated in FIGS. 18 and 19. Each discharge port receptor communicates with electrically actuated four-way valve 76 via an outflow tube 86. A single plastic tube 88 then communictes four-way valve with the fluid pump 90. The four-way valve determines which of the reservoirs will communicate with fluid pump 90 and thereby from which reservoir fluid pump 90 will pump the fluid out through the outflow tube 92 to a spring loaded outflow hose reel 94. Outflow hose reel 94 is similarly configured and operates like the reel of co-pending application Ser. No. 731,897. It keeps the outflow hose 31 from tangling and automatically winds the excess hose about the reel. Hygiene unit connector 29 is secured to the outer end of outflow hose 31 to provide a double locking male connector for the corresponding double grooved female receptor 25 located within catheter housing 19. As shown in FIG. 16, suitable connector retaining clip 96 is secured to the outside of base unit 42 for easy storage when hygiene unit 40 is not in use.

Additionally, mounted on the front plate 112 of base unit 42 are the on-off power button 98, the function selector switch 100, and the step selector dial 102; all control the operations of the hygiene unit as will be later described. Step selector dial 102 indicates the orderly progression through the hygiene steps. Each position of the step selector dial has a corresponding light emitting diode (LED) indicator 104 visible on the front plate 112, and arranged in respective clockwise display around the dial. A suitable jack receptacle 106 is mounted on the back of the unit base for connecting it to a power source. A control unit or microprocessor 108 is electrically connected to the electric motor 110 which drives and controls fluid pump 90 and controls its pumping characteristics. The microprocessor control unit 108 also controls the four-way valve 76 to determine from which of the reservoirs 50, 52, 54 or 56, fluid pump 90 will pump fluid out through outflow hose 31. Thus the microprocessor 108 operates as an "on-board computer", controlling and monitoring the accuracy, progression, timing and completion of all of the unit's functions. The hygiene unit, as an additional precaution, requires coordination between function selector switch 100 and step selector dial 102 to avoid use of the wrong solutions during the hygiene unit's self-cleansing mode.

Description of the Hygiene Process

Figure 19:
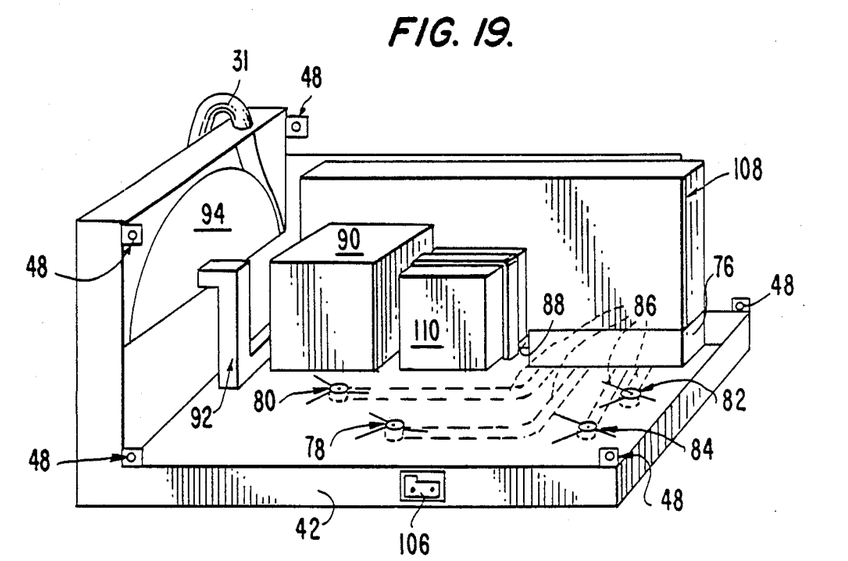
FIG. 19 is a perspective view of the rear of the unit of FIG. 14 with the external housing and reservoirs removed.

The following is a description of a daily regimen process of urinary or other catheter hygiene, as performed using catheter hygiene unit 40 attached to the subject catheter via insertion of connector 29 in receptor 25. All fluids or solutions are pumped from the appropriate reservoir through the hygiene unit 40 and ultimately via connector 29 through channels 4 to ports 6. As these fluids pass through port 6, they enter main urinary lumen 9, cleanse this lumen of urinary debris, bacteria and bacterial growth medium and then exit the catheter at proximal opening 20. Referring to FIGS. 14, 17 and 19, the cleansing of the subject catheter is accomplished in four steps as follows:

Step One: Fifty milliliters of sterile water flowing at approximately forty pounds per square inch are pumped from reservoir 50. Subsequently, one hundred seventy-five milliliters of mucolytic agent solution are pumped from reservoir 56 at a rate of approximately thirty-five milliliters per minute.

Step Two: Fifty milliliters of sterile water are pumped from reservoir 50 at a pressure of approximately forty pounds per square inch. Subsequently, two hundred milliliters of solubilizing agent solution are pumped from reservoir 54 at approximately forty milliliters per minute.

Step Three: Fifty milliliters of sterile water are pumped from reservoir 50 at a pressure of approximately forty pounds per square inch. Subsequently, two hundred fifty milliliters of antiseptic solution are pumped from reservoir 52 at a rate of approximately fifty milliliters per minute.

Step Four: Three hundred fifty milliliters of sterile water are pumped from reservoir 50 at a pressure of approximately forty pounds per squre inch. This constitutes completion of the daily catheter hygiene process and connector 29 is now withdrawn from receptor 25 and the finger tab, slide and hatch cover assembly of housing 19 are returned to their most distal position, closing hatch 27 and returning the catheter to its urinary drainage function mode. Exact composition of solutions used in the catheter hygiene process will be described subsequently, either by amendment or by subsequent application.

The catheter hygiene unit is also equipped with a unit cleansing mode to provide for the periodic cleansing of the unit's reservoirs and other fluid containing parts. The hygiene unit's cleansing mode is comprised of two steps:

Step Five: Twenty-five milliliters of antiseptic solution is placed in each reservoir, 50, 52, 54 and 56. The unit then pumps this twenty-five milliliters of antiseptic solution from each reservoir 50, 52, 54 and 56 respectively. The unit then turns itself off. Antiseptic is one percent benzalkonium chloride (zephiran) solution.

Step Six: Twenty-five milliliters of sterile water are placed in each reservoir 50, 52, 54 and 56. Then the twenty-five milliliters of sterile water are pumped from each reservoir 50, 52, 54 and 56, respectively. The solutions for both cleansing steps V and VI are pumped out through connector 29 into a suitable receptacle, such as a sink with drain. Upon the completion of step VI the hygiene unit automatically turns off.

Description of the Hygiene Unit Operating Process

1. The fluid reservoirs 50, 52, 54 and 56 are first filled prior to plugging the unit in or engaging the power button 98. Hygiene unit 40 is then plugged into a standard 110 V AC outlet via a usual plug and wire power cord assembly attached to jack receptacle 106 at the back of the unit base 42.

2. Spring-loaded power button 98 is placed in its depressed or "on" position. The circuit is completed between power source and indicator light in power button, causing the button to glow red. Each of six cleansing steps (labeled steps I through VI sequentially around the dial) described above and an "off" position have corresponding light emitting diode (LED) indicators 104 arranged sequentially around dial 102. Each indicator 104 flashes when unit 40, as determined by the microprocessor 108 is ready to go to the dial position that corresponds to that flashing indicator, microprocessor 108 notes this and initiates the function of the hygiene step corresponding to the respective indicator. The LED indicator for a step in progress glows constantly (no longer flashing) and then goes off at the completion of that step. When the indicator for the dial position whose step is in progress goes off, this indicates the function corresponding to that dial position has been completed. Immediately thereafter the indicator for the next step will begin flashing until the dial is manually turned or automatically turns to the next step, causing the indicator to glow constantly at the new dial position, corresponding to the new step in progress.

When the main power button 98 is placed in the "on" position the circuit is completed between the power source and microprocessor 108, that controls all functions and steps of hygiene unit 40, as determined by its software program. When microprocessor 108 initially receives power, its program automatically causes the LED indicator corresponding to the "off" position on the step selector dial 102 to flash. If or when the step selector dial is then placed in the "off" position (corresponding to the flashing indicator), a circuit back to the microprocessor 108 is completed, indicating the position of selector dial 102. Microprocessor 108 then completes a circuit to function selector switch 100 and causes the "off" position indicator of the step selector dial to glow constantly, indicating that the circuit to the function selector switch 100 has been completed.

The unit is now ready for funtion selection. If function selector switch 100 is placed in the "catheter" position, a signal is sent to microprocessor 108, which then causes the LED indicator corresponding to step one to begin flashing. If the function selector switch 100 is placed in the "unit" position, a signal is sent to the microprocessor 108 and the microprocessor in turn causes the LED indicator 104 for Step V to begin flashing.

The progression of steps through the hygiene process will now be described with regard to the electronic function of the hygiene unit 40.

Step selector dial 102 is equipped with an internal cog wheel and ratchet assembly (not shown) that permits the dial to be manually turned in a clockwise direction only. This embodiment utilizes a step selector dial 102 that after the dial is manually turned to the flashing indicator 104 for Steps I, V or VI the dial then turns automatically to the next correct position using transistors in a transistor level logic electronic sequence circuit. Microprocessor 108 will only initiate the next appropriate step in the hygiene process and will not do so until step selector dial 102 is turned (manually for Steps I, V or VI or automatically for other steps) to the appropriate corresponding position with a flashing indicator 104.

3. Function selector switch 100 is placed in the "catheter" position and the indicator for step I begins flashing, as directed by the microprocessor 108. When step selector dial 102 is placed at postion Step I, microprocessor 108 receives this information and causes the indicator at position Step I to glow constantly, indicating the initiation of Step I. As Step I is initiated, microprocessor 108 senses the position of the four-way way valve 76 and, if the valve is not open to water reservoir 50, it signals the valve actuator of the valve 76 to open for inflow from the water reservoir. The four-way actuator utilizes a transistor to transistor logic level or other compatible means for control by microprocessor 108.

Subsequently, microprocessor 108 completes the power circuit to the electric motor component 110 of pump 90 and causes it to begin operation at its highest speed, producing a connector 29 outflow of sterile water at approximately forty pounds per square inch. Microprocessor uses a pump interface control circuit to provide the necessary logic level signals to control pump motor 110. Hygiene unit 40 thereby achieves its required outflow rates. All timing and control functions originate in the microprocessor 108 and will be logged by the microprocessor. The microprocessor via its integral timing circuit notes the time that the electric pump motor 110 begins operation and interrupts the power circuit to the pump after the appropriate time has elapsed to allow the outflow of 50 milliliters of sterile water. Then microprocessor 108 interrupts the power circuit to electric pump motor 110. The microprocessor 108 then directs the actuator for valve 76 to close inflow from water reservoir 50 and open for inflow from mucolytic agent reservoir 56. The microprocessor 108 then completes the power circuit to electric motor 110 and causes operation at a speed sufficient to produce a flow of mucolytic agent solution at thirty-five milliliters per minute. Five minutes later, the microprocessor via its integral timing circuit interrupts the power circuit to the electric pump motor 110. As microprocessor 108 now interrupts the power circuit to electric pump motor 110, Step I is completed. The power circuit for the LED indicator for Step I is also interrupted and the indicator for Step I goes off. Microprocessor 108 initiates a power circuit causing the LED indicator for Step II to begin flashing, indicating that Step I has been completed and that the hygiene unit is ready to begin Step II.

4. Subsequently, the step selector dial 102 automatically moves to position II, the microprocessor receives this information and causes the LED indicator for Step II to glow constantly, indicating the initiation of Step II. As Step II is initiated, microprocessor 108 signals four-way valve 76 to close off the outflow from reservoir 56 and open the outflow from sterile water reservoir 50. Subsequently, microprocessor 108 completes the power circuit to electric pump motor 110, causing it to operate at its highest speed, producing outflow of sterile water at approximately forty pounds per square inch. The microprocessor via its integral timing circuit notes the time that electric pump motor 110 begins operation and interrupts the power circuit to pump motor 110 after the appropriate time has elapsed to allow the outflow of 50 milliliters of sterile water. Then microprocessor 108 interrupts the power circuit to electric pump motor 110. The microprocessor 108 then directs the actuator for valve 76 to close inflow from water reservoir 50 and open for inflow from solubilizing agent solution reservoir 54. The microprocessor 108 then completes the power circuit to electric motor 110 and causes operation at a speed sufficient to produce a flow of solubilizing agent solution at forty milliliters per minute. five minutes later, the microprocessor via its integral timing circuits, interrupts the power circuit to the electric pump motor 110. As microprocessor 108 interrupts the power circuit to electric pump motor 110, Step II is completed and the power circuit for the steady glow of the LED indicator corresponding to Step II is interrupted, causing the LED indicator for Step II to extinguish. Simultaneously, the microprocessor's power circuit to the LED indicator for Step III is activated and this indicator begins flashing, indicating that the unit is ready for Step III.

5. Subsequently, the step selector dial 102 automatically moves to position III, microprocessor 108 receives this information and causes the LED indicator 104 for Step III to glow constantly, indicating the initiation of Step III. As Step III is initiated, the microprocessor signals the actuator for the four-way valve 76 to close off the outflow from reservoir 54 and open the outflow from sterile water reservoir 50. The microprocessor 108 then completes the power circuit to electric pump motor 110, causing it to operate at its highest speed, producing a connector outflow of sterile water at approximately forty pounds per square inch. The microprocessor 108, via its integral timing circuit, notes the time that electric pump motor 110 begins operation and interrupts the power circuit to the pump after the appropriate time has elapsed to allow the outflow of fifty milliliters of water. Then microprocessor 108 interrupts the power circuit to electric pump motor 110. The microprocessor 108 then directs the actuator for valve 76 to close inflow from water reservoir 50 and open for inflow from antiseptic solution reservoir 52. The microprocessor then completes the power circuit to electric motor 110 and causes operation at a speed sufficient to produce a flow of antiseptic solution at fifty milliliters per minute. Five minutes later, the microprocessor via its integral timing circuit, interrupts the power circuit to the electric pump motor 110. As microprocessor 108 interrupts the power circuit to the electric pump motor, Step III is completed and the power circuit for the steady glow of the LED indicator for Step III is interrupted, causing the indicator for Step III to go off. Simultaneously, the microprocessor's power circuit to the LED indicator for Step IV is activated and this indicator begins flashing, indicating that the unit is ready for Step IV.

6. Subsequently, the step selector dial 102 automatically moves to position Step IV, microprocessor 108 receives this infomation and causes the LED indicator 104 for Step IV to glow constantly, indicating the initiation of Step IV. As Step IV is begun, the microprocessor signals the actuator for the four-way valve 76 to close off the outflow from reservoir 52 and open the outflow from sterile water reservoir 50. The microprocessor 108 then completes the power circuit to electric pump motor 110, causing it to operate at its highest speed, producing a connector outflow of sterile water at approximately forty pounds per square inch. The microprocessor via its integral timing circuit, notes the time that electric pump motor 110 begins operation and interrupts the power circuit to the pump after the appropriate time has elapsed to allow the outflow of three hundred fifty milliliters of sterile water. As the microprocessor interrupts the power circuit to the electric pump motor, Step IV is completed and the power circuit for the steady glow of the LED indicator for Step IV is interrupted, causing the indicator for Step IV to go off. At the completion of Step IV, microprocessor 108 initiates a circuit that signals main power button 98 to return to the "off" position. The main power circuit between the power source jack 106 and the main power button 98 is interrupted, turning the entire hygiene unit 40 off, as a remainder to unplug the unit for refilling the reservoirs 50, 52, 54 and 56 for the next cleansing process.

7. To facilitate cleaning the hygiene unit 40 itself, an additional position of the function selector switch 100 is provided and labelled "Unit". As a safety feature, to avoid inappropriate use of Steps V or VI during catheter hygiene, the hygiene unit 40 will not proceed through Steps V or VI unless the function selector switch 100 has been shifted to the "Unit" position and the step selector dial 102 has been manually turned to the appropriate Step V or VI position. Steps V and VI proceed in an electronically similar fashion as described above for Steps I through IV, including a pause and an automatic return of the main power button 98 to the "off" position between Steps V and VI. During Steps V and VI electric pump motor 110 is operated at its highest speed to produce a connector 29 outflow of approximately forty pounds per square inch.

When hygiene unit 40 is turned on by activating main power button 98 and function selector switch 100 is placed in the "Unit" position, the LED indicator corresponding to Step V on the step selector dial begins flashing. The hygiene unit's self-cleaning mode allows a cleaning solution of one percent benzalkonium chloride aqueous solution (one percent zephiran solution) to be flushed through all fluid containing reservoirs, lines, hoses and the connector 29 of the hygiene unit. This cleaning of the hygiene unit is completed by subsequently pumping sterile water through all the fluid containing portions of the unit, during electronically similar Step VI.

To begin Step V, the step selector dial is manually turned to the Step V position, microprocessor 108 receives this information and causes the indicator for Step V to glow constantly, indicating the initiation of Step V. As Step V is initiated, the microprocessor signals the four-way valve 76 to sequentially open and subsequently close the outflow from each reservoir 50, 52, 54 and 56, respectively, one reservoir outflow at a time. As each reservoir's outflow is opened the motor 110 is activated for a period long enough to pump twenty-five milliliters of one percent zephiran solution from each reservoir in turn. After each reservoir's zephiran load is discharged, the microprocessor 108 inactivates the power circuit to motor 110 until the outflow from the discharged reservoir is closed by actuator for valve 76 and outflow for the next reservoir is opened by actuator for valve 76.

At the completion of Step V, the microprocessor initiates a circuit that signals main power button 98 to return to the off position. The hygiene unit's main power circuit is thus interrupted and the entire hygiene unit 40 is turned off.

An alternative embodiment, in which daily irrigation of the patient's bladder is performed (using any fluid or solution) subsequent to a similar dialy catheter hygiene program as described herin, is considered to be within the scope of the present invention.

In summary, dialy catheter hygiene using the catheter hygiene unit and methods of the present invention will provide catheterized patients with improved hygiene, greater opportunity for the prevention of urinary tract infection and associated sepsis.

From the foregoing detailed descriptions, it will be evident that there are a number of changes, adaptions, and modifications of the present invention that come within the province of those persons having ordinary skill in the art to which the aforementioned invention pertains. However, it is intended that all such variations not departing from the spirit of the invention be considered as within the scope thereof as limited only by the appended claims.

I claim:

1. An apparatus for insertion into a human body for draining liquid and liquid with suspended solid particles from an area of that human body and for cleansing the apparatus throughout its length comprising:
 a container shaped and sized to be inserted into said area so that said liquid and liquid with suspended solid particles from said area may be collected in and drained from said container, a collection lumen within said container for receiving and draining said liquids, at least one port in said container to provide liquid communication between said lumen in said container and said area, valve means operably connected to said container for selectively and reversibly opening and closing said port to control passage of said liquids from said body area into said lumen of said container, and cleansing means for periodically cleansing and flushing said lumen with cleansing fluids to cleanse, disinfect and decontaminate said lumen without exposing said body area to said cleansing, disinfecting and decontaminating fluids and without removal of said container from said body, said cleansing means having an outlet positioned into said lumen such that said cleansing fluids cleanse said lumen distal to said port, and whereby said lumen is cleansed throughout its length for healthy continued retention in said body.

2. The apparatus of claim 1 including,
said apparatus being a urinary catheter.

3. The apparatus of claim 2 including,
said catheter being cylindrically shaped.

4. The apparatus of claim 2 including,
said container being cylindrically shaped and having a blunt, closed distal end.

5. The apparatus of claim 4 including,
said ports being plural and positioned proximate to said distal end.

6. The apparatus of claim 2 including,
said liquid and liquid with suspended solid particles being urine, urinary debris, bacterial growth medium and bacteria.

7. The apparatus of claim 1 including,
said area being the urinary bladder.

8. The apparatus of claim 1 including,
said container being a urinary catheter with distal and proximal ends, and said distal end of said catheter being placed in said urinary bladder, using accepted aseptic technique.

9. The apparatus of claim 8 including,
said means of periodically cleansing and flushing said lumen including a urinary catheter hygiene unit having selectively operable means for applying preselected cleansing fluids to said lumen.

10. The apparatus of claim 9 including,
a balloon positioned on said catheter for reversible inflation with inflation means.

11. The apparatus of claim 10 including,
said inflation means comprising a balloon inflation channel in said catheter for inflation of said balloon.

12. The apparatus of claim 11 including,
said inflation means further comprising
a twist valve means connected to said channel to control inflation of said balloon.

13. The apparatus of claim 9 including,
said hygiene unit comprising:
a fluid pump,
a plurality of liquid reservoirs containing cleansing liquids, conduit means providing fluid communication with said reservoirs and being connected to said pump,
fluid connecting means connecting said reservoirs to said collection lumen for cleansing said collection lumen.

14. The apparatus of claim 13 including,
second valve means selectively connecting each said reservoir to said pump and positioned within the fluid flow path between each said reservoir and said pump.

15. The apparatus of claim 14 including,
a valve actuating means for controlling said selective connections of said second valve means.

16. The apparatus of claim 15 including,
a microprocessor controlling said valve actuating means.

17. The apparatus of claim 16 including,
a function selector switch means,
a power on and off switch or button means and
a step selector dial means operatively connected to said microprocessor,
said microprocessor electrically connected to said power switch means, to said function selector switch means, to said selector dial means, and said valve actuating means.

18. The apparatus of claim 17 including,
said microprocessor being adapted to monitor the position of said power switch means and said step selector switch means and to cause said fluid pump to pump liquid selectively from said second valve means according to a predetermined sequence.

19. The unit of claim 14 including,
said valve means comprising a four-way valve with four inflow legs, each leg connected to an outflow tube from each of the said reservoirs and an outflow leg connected to said connector means and said fluid pump being interposed within the fluid path between said outflow leg and said connector means.

20. The unit of claim 19 including,
said microprocessor controlling means being adapted to cause said pump means to pump fluids from said reservoirs at a variety of flow intensities with either a constant or a pulsating flow.

21. The unit of claim 20 including,
said unit being supplied with 110 V alternating current electrical power using a standard wall socket compatible plug, power cord, power jack and jack receptacle assembly on said unit as commonly known to those familiar with the present art.

22. The unit of claim 21 including,
a power button having an "on" and "off" position,
a function selector switch having a "catheter" and a "unit" position,
a step selector dial having seven dial positions arranged sequentially clockwise around said dial,
said dial positions representing respectively an "off" position and a position for each of Steps I, II, III, IV, V and VI,
each of said power button, function selector switch and step selector dial being electrically connected and controlled by said microprocessor controlling means.

23. The unit of claim 22 including,
said step selector dial positions each having corresponding light emitting diode (LED) indicators arranged sequentially around said dial.

24. The unit of claim 23 including,
said light emitting diode indicators each having an intermittent flashing mode of operation and a constantly glowing mode of operation,
said flashing mode corresponding to said a step determined by said microprocessor to be ready for initiation, said constantly glowing mode corresponding to a step determined by said microprocessor controlling means to be currently in progress.

25. The unit of claim 24 including, said predetermined sequences including, said controlling means sensing position of said power button as being in said "on" position, said controlling means sensing position of said function selector switch as being in said "catheter" position, said controlling means sensing position of said step selector dial as being in said Step I position, said LED indicator corresponding to said Step I dial position glows constantly, said controlling means directs said valve means to open valve for inflow from a water reservoir and thereafter directs said pump to cause outflow of fifty milliliters of a sterile water from said connector at a pressure of approximately forty pounds per square inch, thereafter said controlling means directs said pump to cease operation and directs said valve actuator to close valve inflow from said water reservoir and open valve inflow from a mucolytic agent reservoir and thereafter directs said pump to cause outflow of said mucolytic agent solution from said connector at a constant flow of approximately thirty-five milliliters per minute for a duration of five minutes, thereafter said controlling means directs said pump to cease operation and directs said Step I indicator to cease glowing and directs said Step II indicator to begin flashing, thereafter said controlling means directs said dial to automatically turn clockwise to said position for said Step II and directs said Step II indicator to glow constantly, thereafter said controlling means directs said valve actuator to close said inflow from said mucolytic agent reservoir and open said inflow from said water reservoir and thereafter directs said pump to cause outflow of fifty milliliters of said sterile water from said connector at a pressure of approximately forty pounds per square inch, thereafter said controlling means directs said pump to cease operation and directs said valve actuator to close valve inflow from said water reservoir and open valve inflow from said solubilizing agent reservoir and thereafter directs said pump to cause outflow of said solubilizing agent solution from said connector at a constant flow of approximately forty milliliters per minute for a duration of five minutes, thereafter said controlling means directs said pump to cease operation and directs said Step II indicator to cease glowing and directs said Step III indicator to begin flashing, thereafter said controlling means directs said dial to automatically turn clockwise to said position for said Step III and directs said Step III indicator to glow constantly, thereafter said controlling means directs said valve actuator to close said inflow from said solubilizing agent reservoir and open said inflow from said water reservoir and thereafter directs said pump to cause outflow of fifty milliliters of said sterile water from said connector at a pressure of approximately forty pounds per square inch, thereafter said controlling means directs said pump to cease operation and directs said valve actuator to close valve inflow from said water reservoir and open valve inflow from said antiseptic solution reservoir and thereafter directs said pump to cause outflow of said antiseptic solution from said connector at a constant flow of approximately fifty milliliters per minute for a duration of five minutes, thereafter said controlling means directs said pump to cease opertion and directs said Step III indicator to cease glowing and directs said Step IV indicator to begin flashing, thereafter said controlling means directs said dial to automatically turn clockwise to said position for said Step IV and directs said Step IV indicator to glow constantly, thereafter said controlling means directs said valve actuator to close said inflow from said solubilizing agent reservoir and open said inflow from said water reservoir and thereafter directs said pump to cause outflow of three hundred fifty milliliters of said sterile water from said connector at a pressure of approximately forty pounds per square inch, thereafter said controlling means directs said pump to cease operation and directs said power button to go to said "off" position causing said unit to cease operation.

26. The unit of claim 25 including, said predetermined sequences including, said controlling means sensing position of said power button as being in said "on" position, said controlling means sensing position of said function selector switch as being in said "unit" position, said controlling means sensing position of said step selector dial as being in said Step V position, said indicator corresponding to said Step V dial position glows constantly, said controlling means directs said valve actuator to open valve for inflow from said water reservoir and thereafter directs said pump to cause outflow of twenty-five milliliters of one percent benzalkonium sodium solution for unit cleansing from said connector at a pressure of approximately forty pounds per square inch, thereafter said controlling means directs said pump to cease operation and directs said valve actuator to close valve inflow from said water reservoir and open valve inflow from said mucolytic agent reservoir and thereafter directs said pump to cause outflow of twenty-five milliliters of said cleansing solution from said connector at a pressure of approximately forty pounds per square inch, thereafter said controlling means directs said pump to cease operation and directs said valve actuator to close valve inflow from said mucolytic agent reservoir and open valve inflow from said solubilizing agent reservoir and thereafter directs said pump to cause outflow of twenty-five milliliters of said cleansing solution from said connector at a pressure of approximately forty pounds per square inch, thereafter said controlling means directs said pump to cease operation and directs said valve actuator to close valve inflow from said solubilizing agent reservoir and open valve inflow from said antiseptic solution reservoir and thereafter directs said pump to cause outflow of twenty-five milliliters of said cleansing solution from said connector at a pressure of approximatley forty pounds per square inch, thereafter said controlling means directs said pump to cease operation and directs said power button to go to said "off" position causing said unit to cease operation.

27. The unit of claim 26 including, said predetermined sequences including, said controlling means sensing position of said power button as being in said "on" position, said controlling means sensing position of said function selector switch as being in said "unit" position, said controlling means sensing position of said step selector dial as being in said Step VI position, said indicator corresponding to said Step VI dial position glows constantly, said controlling means directs said valve actuator to open valve for inflow from said water reservoir and thereafter directs said pump to cause outflow of twenty-five milliliters of sterile water from said connector at a pressure of approximately forty pounds per square inch, thereafter said controlling means directs said pump to cease operation and directs said valve actuator to close valve inflow from said water reservoir and open valve inflow from said mucolytic agent reservoir and thereafter directs said pump to cause outflow of twenty-five milliliters of said sterile water from said connector at a pressure of approximately forty pounds per square inch, thereafter said controlling means directs said pump to cease operation and directs said valve actuator to close valve inflow from said mucolytic agent reservoir and open valve inflow from said solubilizing agent reservoir and thereafter directs said pump to cause outflow of twenty-five milliliters of said sterile water from said connector at a pressure of approximately forty pounds per square inch, thereafter said controlling means directs said pump to cease operation and directs said valve actuator to close valve inflow from said solubilizing agent reservoir and open valve inflow from said antiseptic solution reservoir and thereafter directs said pump to cause outflow of twenty-five milliliters of sterile water from said connector at a pressure of approximately forty pounds per square inch, thereafter said controlling means directs said pump to cease operation and directs said power button to go to said "off" position causing said unit to cease operation.

28. The apparatus of claim 8 including, an opening at said proximal end for the discharge of collected urine from said collection lumen.

29. The apparatus of claim 8 including, said cleansing means including at least one cleansing fluid outlet opening into said collection lumen at a location on the distal side of said port.

30. The apparatus of claim 29 including, at least one cleansing fluid channel parallel to said collection lumen and in fluid communication with said cleansing fluid outlet.

31. The apparatus of claim 8 including, an opening at said proximal end of said collection lumen including a one way flow valve to prevent reflux of discharged urine back into said collection lumen.

32. The apparatus of claim 8 including, said container being cylindrically shaped and having a blunt, closed distal end, and said ports being plural and positioned proximate to said distal end.

33. The apparatus of claim 8 including, said container being cylindrically shaped and having a blunt, closed distal end, said ports being plural and positioned proximate to said distal end, a balloon positioned on said catheter for reversible inflation, and a balloon inflation channel on said catheter for inflation of said balloon.

34. The apparatus of claim 8 including, said container being cylindrically shaped and having a blunt, closed distal end, said ports being plural and positioned proximate to said distal end, a balloon positioned on said catheter for reversible inflation, a balloon inflation channel on said catheter for inflation of said balloon, a twist valve means connected to said channel to control inflation of said balloon, and an opening at said proximal end for the discharge of collected urine from said collection lumen.

35. The apparatus of claim 34 including, said means of periodically cleansing and flushing said lumen including a urinary catheter hygiene unit.

36. The catheter of claim 8 including, said valve means of reversibly closing said urine inflow ports including a urine inflow port occlusion slide.

37. The catheter of claim 36 including, each said urine inflow port occlusion slide being a generally flat enlongated and thin object that can be moved proximally or distally along a channel for this purpose with said channel being located longitudinally within the wall of said catheter.

38. The catheter of claim 37 including, said slide having a proximal and a distal end corresponding to said catheter's said proximal and distal ends, said slide being formed with an opening near said slide's distal end, said slide opening being shaped and sized with dimensions similar to said urine inflow ports, said slide channel and said slide being shaped and located so that said slide opening aligns with and allows passage of urine through said urine port when said slide is advanced to a most distal position within said channel.

39. The catheter of claim 38 including, said slide channel being shaped and located and said distal end of said slide being shaped so that said distal end aligns with and completely occludes said cleansing fluid inflow port when said slide is advanced to said most distal position within said channel.

40. The catheter of claim 39 including, said slide channel and said slide being shaped and located so that said slide opens said cleansing fluid inflow port and allows passage of cleansing fluids through said port when said slide is pulled to a most proximal position within said slide channel.

41. The catheter of claim 40 including, said slide channel and said slide being shaped and located so that said slide completely occludes said urine inflow port when said slide is pulled to said most proximal position within said slide channel.

42. The catheter of claim 41 including,
a receptor being located within a housing just distal to said catheter's said proximal end.

43. The catheter of claim 42 including,
a housing having an upper surface with a hatch opening aligned with said receptor.

44. The catheter of claim 43 including,
said hatch having a sliding cover located within said housing,
said cover reversibly providing access to said receptor,
said cover blocking access to said receptor when said cover is moved to a most distal position within said housing, and
said cover providing access to said receptor when said cover is moved to a most proximal position within said housing.

45. The catheter of claim 44 including,
said cover having a manual control means,
said port occlusion slides having a manual control means functionally integrated with and attached to said cover control means so that said most proximal position of said port occlusion slides correspond exactly with said most proximal position of said hatch cover, and
said most distal position of said port occlusion slides correspond exactly with said most distal position of said hatch cover.

46. The apparatus of claim 1 including,
said liquid and liquid with suspended solid particles being wound tissue exudate, tissue debris, bacterial growth medium and bacteria.

47. The apparatus of claim 1 including,
said cleansing means including a valved opening proximally positioned for controlling flow of said cleansing fluids toward said distal end.

48. The apparatus of claim 47 including,
said valve means including a safety means operatively connected between said valved opening and said outlet to prevent the possibility of cleansing fluids exiting from said outlet into the human body.

49. The apparatus of claim 47 including,
said safety means including an elongated slide connected to said valved opening and said outlet for movement to close said outlet and simultaneously open said valved opening whereby to flush said lumen with cleansing fluids without permitting said fluids from exiting the human body.

50. The apparatus of claim 49 including,
said slide having an aperture sized to correspond to said port in said container.

51. The apparatus of claim 47 including,
said valve means including a safety means operatively connected between said valve opening and said outlet to prevent the possibility of cleansing fluids exiting from said outlet into the human body, and
said safety means including an elongated slide connected to said valve opening and said outlet for movement to close said outlet and simultaneously open said valved opening whereby to flush said lumen with cleansing fluids without permitting said fluids from exiting the human body.

52. The apparatus of claim 47 including,
the valved opening being a hatch cover means covering the proximal end of a cleansing channel included within said cleansing means and extending the approximate length of said lumen.

53. The apparatus of claim 47 including,
said valve means including a safety means operatively connected between said valved opening and said outlet to prevent the possibility of cleansing fluids exiting from said outlet into the human body,
said safety means including an elongated slide connected to said valved opening and said outlet for movement to close said outlet and simultaneously open said valved opening whereby to flush said lumen with cleansing fluids without permitting said fluids from exiting the human body,
said slide having an aperture sized to correspond to said port in said container, and
the valved opening being a hatch cover means covering the proximal end of a cleansing channel included within said cleansing means and extending the approximate length of said lumen.

* * * * *